United States Patent
Flohr et al.

(10) Patent No.: US 8,634,625 B2
(45) Date of Patent: Jan. 21, 2014

(54) METHOD FOR THE REDUCTION OF IMAGE ARTIFACTS, IN PARTICULAR OF METAL ARTIFACTS, IN CT IMAGE DATA

(75) Inventors: Thomas Flohr, Uehlfeld (DE);
Bernhard Krauβ, Burgthann (DE);
Rainer Raupach, Heroldsbach (DE);
Bernhard Schmidt, Nürnburg (DE)

(73) Assignee: Siemens Aktiengesellschaft, Munich (DE)

( * ) Notice: Subject to any disclaimer, the term of this patent is extended or adjusted under 35 U.S.C. 154(b) by 213 days.

(21) Appl. No.: 13/107,302

(22) Filed: May 13, 2011

(65) Prior Publication Data
US 2011/0280458 A1 Nov. 17, 2011

(30) Foreign Application Priority Data
May 17, 2010 (DE) .......................... 10 2010 020 770

(51) Int. Cl.
*G06K 9/00* (2006.01)
(52) U.S. Cl.
USPC .......................................... 382/131; 382/128
(58) Field of Classification Search
None
See application file for complete search history.

(56) References Cited

U.S. PATENT DOCUMENTS

| 4,611,341 | A * | 9/1986 | Brody | 378/98.11 |
| 7,639,773 | B2 * | 12/2009 | Imai | 378/5 |
| 7,856,134 | B2 * | 12/2010 | Ruhrnschopf et al. | 382/131 |
| 2006/0067457 | A1 * | 3/2006 | Zamyatin et al. | 378/4 |
| 2010/0014737 | A1 * | 1/2010 | Ruhrnschopf et al. | 382/131 |

FOREIGN PATENT DOCUMENTS

DE 102008030552 A1 12/2009

OTHER PUBLICATIONS

Gleason et al.; Reconstruction of Multi-Energy X-Ray Computed Tomography Images of Laboratory Mice IEEE Transactions on Nuclear Science, vol. 46, Issue 4, Aug. 1999 pp. 1081-1086; Magazine; 1999.
Schmidt et al.: "Optimal "image-based" weighting for energy-resolved CT", Med. Physics, vol. 36, Iss. 7, 2009, p. 3018-3027; Others; 2009.
Behrendt et al.: "Image Fusion in Dual Energy Computed Tomography—effect on contrast enhancement, signal-to-noise ratio and image Quality in computed tomography angiography", Investigative radiology, vol. 44, No. 1, Jan. 2009, p. 1-6; Others; 2009.

* cited by examiner

*Primary Examiner* — Nancy Bitar
(74) *Attorney, Agent, or Firm* — Harness, Dickey & Pierce, P.L.C.

(57) ABSTRACT

A method is disclosed for the reduction of image artifacts, in particular metal artifacts, during the generation of computed tomography image data of an object. In at least one embodiment of the method, two CT image data sets are generated with different medium x-ray energies. By way of a weighted combination of the two CT image data sets, a new image data set is calculated. The weighting factor employed in the weighted combination is here selected in such a way that the image artifacts in the new CT image data set are significantly reduced compared with the image artifacts in the two original CT image data sets. In this way it is possible in a simple manner significantly to reduce in particular metal artifacts in CT images.

3 Claims, 2 Drawing Sheets

METHOD FOR THE REDUCTION OF IMAGE ARTIFACTS, IN PARTICULAR OF METAL ARTIFACTS, IN CT IMAGE DATA

PRIORITY STATEMENT

The present application hereby claims priority under 35 U.S.C. §119 on German patent application number DE 10 2010 020 770.5 filed May 17, 2010, the entire contents of which are hereby incorporated herein by reference.

FIELD

At least one embodiment of the present invention generally relates to a method for the reduction of image artifacts, in particular of metal artifacts, during the generation of computed tomography (CT) image data of an object.

BACKGROUND

Image artifacts can occur in CT images as a result of different effects. One of these effects is attributable to so-called beam hardening, which is caused by the energy-dependent attenuation of x-ray beams. Beam hardening occurs in CT scanners, because their x-ray tubes emit no monoenergetic x-rays but a broader x-ray spectrum. With the increasing thickness of the objects being irradiated, the low-energy portions of this x-ray spectrum are more strongly absorbed than the high-energy parts. A higher proportion of hard, high-energy radiation thus reaches the detector and dark zones arise in the image. Metallic implants too result in beam hardening. Excessively strong image artifacts may, for example, occur in the form of light and dark stripes in the vicinity of the metal.

SUMMARY

In at least one embodiment of the present invention, a method is specified for the generation of CT images, with which metal artifacts of this kind in the images can be reduced in a simple manner, especially in the field of medical imaging.

Advantageous embodiments of the method are the subject matter of the dependent claims or are evident from the following description and the example embodiment.

In the proposed method of at least one embodiment, two computed tomography scans are made of the object or object volume of interest simultaneously or at short intervals with respectively different medium x-ray energies. This can take place with a so-called dual-energy CT scanner or also with an appropriately equipped C-arm system. The different medium x-ray energies can here be generated by way of different high voltage at the correspondingly used x-ray tube or tubes of the imaging system. Alternatively the different x-ray energy spectrums can also be generated with different filters or energy-selective detectors can be employed.

In one particular advantage, a CT scanner is disclosed with two imaging systems comprising, in each case, an x-ray tube and an x-ray detector, in which the two x-ray tubes are operated with different tube voltage. In this way the two CT scans can be performed simultaneously.

Finally, two CT image data sets are generated from the raw data thereby obtained in a known manner, for example using the filtered back projection technique. Each CT image data set is thus assigned to a different medium x-ray energy or as the case may be a different x-ray energy spectrum or different tube voltage, which can, for example, be 80 kV and 140 kV.

It was here recognized that metal parts present in the object volume cause very similar image artifacts in the CT images generated with different medium x-ray energy. The image artifacts here differ essentially in their strength.

This finding is exploited in at least one embodiment of the present method, in order to reduce the image/metal artifacts. To this end a new CT image data set is calculated on the basis of the image data of the two CT image data sets by way of a weighted combination of these two CT image data sets. The weighting factor used in the weighted combination is selected in such a way that the image artifacts in the new CT image data set are reduced compared with the image artifacts in the two original CT image data sets. One or more images of the new CT image data set are here displayed to the user.

In this way, image artifacts, as are in particular caused by metal parts present in the of interest object volume, can be significantly reduced by way of simple post-processing of the image data. This applies for example to metallic implants in medical imaging, for example to joint implants, which can lead to significant image artifacts in CT images.

In one embodiment of the proposed method, the weighted combination of the two CT image data sets takes place by way of a weighted subtraction of these two data sets. Here the items of image data, that is to say gray or intensity values for in each case identical pixels or voxels are subtracted from each other, in order to obtain the intensity or gray value for the corresponding pixel or voxel of the new CT image data set. The subtraction here takes place for example working from the CT image data set of the higher medium x-ray energy, from which the CT image data set with the lower medium x-ray energy with the corresponding weighting factor is subtracted. The subtraction can of course also take place based on the image data set with the lower medium x-ray energy.

The appropriate weighting factor can here be determined in advance empirically or by way of corresponding model calculations. In an advantageous embodiment of the proposed method the user has the possibility of changing the weighting factor when examining one or more images of the new CT image data set and here simultaneously examining the change in the images. In this way it is possible in a simple manner to minimize undesired image artifacts, for example interactively via a slider control for the weighting factor represented on the display screen.

In a further, preferred embodiment of the proposed method, a monoenergetic CT image data set is calculated as the new CT image data set from the two CT image data sets with different medium x-ray energies. The x-ray energy for which this monoenergetic CT image data set is calculated, is here set such that the undesired image artifacts are significantly reduced compared with the original image data sets.

The calculation of a monoenergetic CT image data set from CT image data sets with different medium x-ray energies is fundamentally familiar. For this purpose there are commercially available modules which carry out this calculation automatically. The inventors of the present method have however recognized that by way of the suitable selection of the energy of the monoenergetic CT image data set, a marked reduction in the image artifacts caused by metal parts is achieved. In the case of CT scanners with x-ray tubes which—in dual-energy systems—are operated in the voltage range between 80 kV and 140 kV, a reduction for example in the energy range between 120 and 130 keV can occur. This does, however, depend on the properties of the object volume of which the CT image scans are made.

This technique of calculating a monoenergetic CT image data set from two CT image data sets with different medium x-ray energies likewise represents a weighted combination of the two image data sets. Initially, a basis material decomposition of the two CT image data sets, for example into water proportion and bone proportion, is performed here. On the basis of the known energy-dependent x-ray attenuation coefficients of these two materials/substances, the desired CT image data set for each desired energy can then be calculated by means of the corresponding addition of the proportions of these two materials with an energy-dependent weighting factor.

In this preferred embodiment of the proposed method too, one or more CT images of the new CT image data set are preferably displayed to the user on a display screen, where the user can change the selected energy, for example interactively via a slide control on the display screen, and recognize the result of the change immediately or in the CT image or images represented. The user can thus achieve minimizing of the unwanted image artifacts in a simple manner.

The proposed method is preferably performed on an image analysis station of a dual-energy CT scanner, which has an image analysis module embodied for execution of the method.

BRIEF DESCRIPTION OF THE DRAWINGS

The method is once again explained briefly below on the basis of an exemplary embodiment and in conjunction with the drawings, wherein.

DETAILED DESCRIPTION OF THE EXAMPLE EMBODIMENTS

Figure 1:
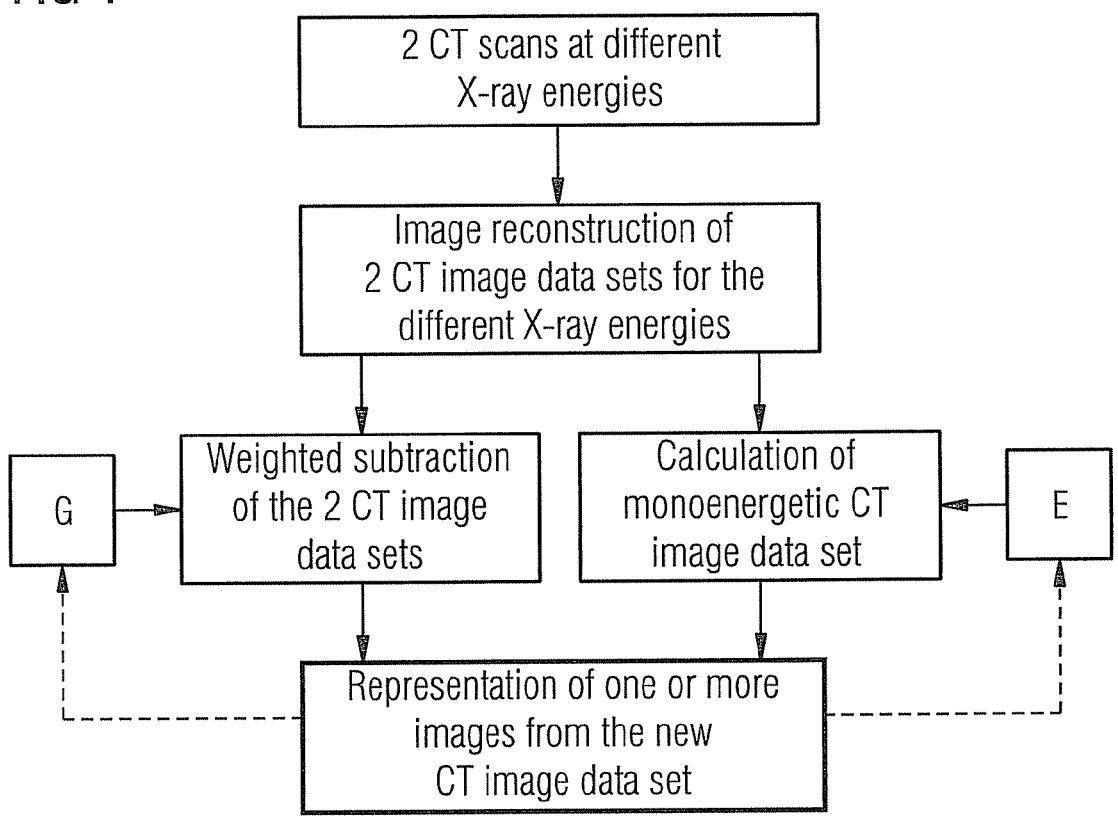
FIG. 1 shows a flow-chart with individual method steps of an example embodiment of the proposed method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the present example CT images of an object phantom are created, in which structures for the schematic mapping of the hip bone and of the two thigh bones are contained, wherein one of the thigh bone structures contains a metallic joint implant.

Two CT scans of the object volume are performed with a dual-energy-CT scanner with different medium x-ray energies. The two scans are here performed simultaneously with the two separate imaging systems, which are operated with different medium x-ray energies. The x-ray tubes of the first imaging system are operated with a low tube voltage of 80 kV and thus a low medium x-ray energy, while the x-ray tubes of the second imaging system are operated with a higher tube voltage of 140 kV and thus a higher medium x-ray energy.

Two CT image data sets $I_1$, $I_2$ are calculated in a known manner by way of filtered back projection from the two CT scans, which have been simultaneously recorded during a CT scan. $I_1$ here corresponds to the image data set at low tube voltage, and $I_2$ the image data set at high tube voltage. A basis material decomposition is then performed with these two image data sets, the following equation being applied for the value x of each pixel or voxel of the respective image data set:

$$w_1 = a + f_1 * c$$

$$x_2 = a + f_2 * c.$$

The two parameters a and c can be determined by way of these two equations for the gray or intensity values $x_1$ of the pixels or voxels of the first image data set $I_1$ and the gray or intensity values $x_2$ of the pixels or voxels of the second image data set $I_2$. In this case a basis material decomposition into a water proportion a and a bone proportion c is carried out, so that one data set with the water proportion and one data set with the bone proportion is thereby obtained. The dependent values for $f_1$ and $f_2$ of the x-ray energy used (for example Index 1 for low kV and Index 2 for high kV) can be derived from tables specifying the energy-dependent x-ray attenuation of bones. From the two distributions thus obtained it is then possible to calculate a CT image $I_E$ for each energy:

$$x_E = a + c * g(E).$$

The weighting factor g(E) represents the relationship between a bone concentration c and the resultant contribution to the CT value depending on the energy. This relationship can likewise be taken from tables.

In the proposed method the energy or as the case may be weighting factor g(E) are selected such that the image artifacts in the calculated monoenergetic CT image data set caused by the metallic artificial joint are significantly reduced, preferably minimized compared with the CT image data sets originally recorded. The corresponding CT image or images of this newly calculated CT image data set $I_E$ is/are presented to the user on a display screen. The course of this method can be seen in schematic form in FIG. 1.

FIG. 1 shows the second alternative method as well, in which a new CT image data set $I_E$ is obtained from the two original CT image data sets by means of weighted subtraction, in which the image artifacts caused by the artificial joint are likewise reduced. To this end the gray or intensity values of the pixels or voxels of the individual image data sets $I_2$ are subtracted from each other in an appropriate manner:

$$x_E = (x_2 - x_{2,base}) - g * (x_1 - x_{1,base}).$$

The weighting factor g is here likewise selected in the above-mentioned manner. $x_{i,base}$ here ensures that that the subtraction takes place at the HU level of the soft tissue and thus only the artifacts are subtracted from each other.

In the preferred embodiment, this weighting factor g or the energy E or g(E) are in the first alternative changed by the user via an interactive setting facility on the display screen in such a way that the new CT image obtained with the weighting factor currently selected in each case exhibits the desired reduction in the image artifacts. The user can directly track the effect of the change in this weighting factor on the CT image on the display screen. This enables very simple setting options and reduction of the image artifacts in the CT image represented.

Figure 2:
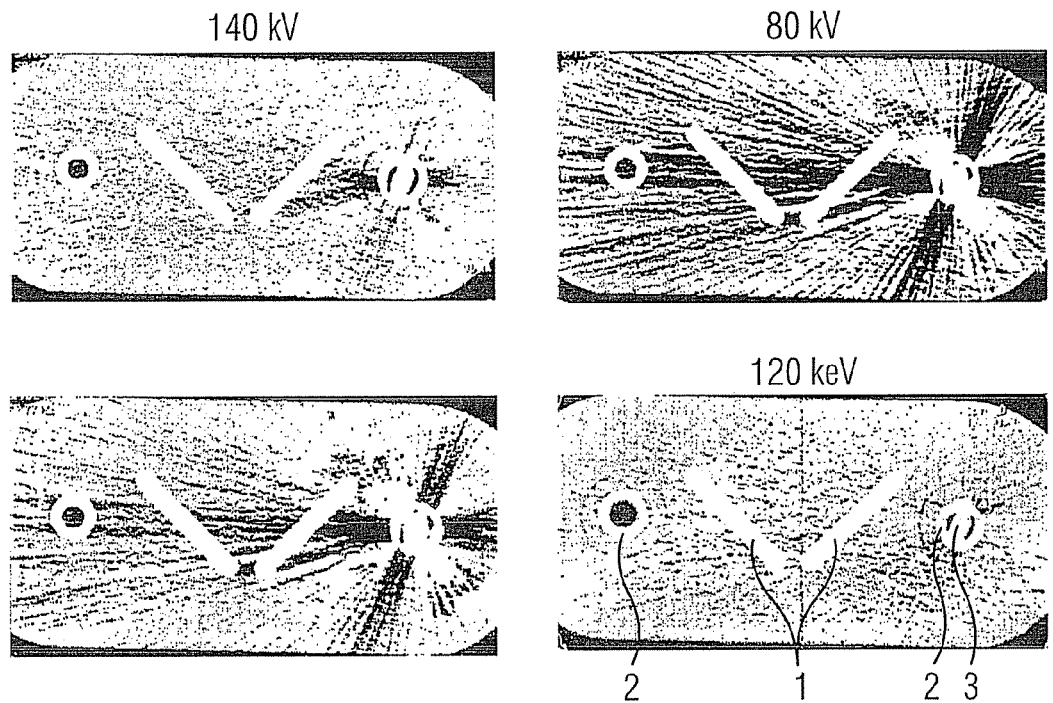
FIG. 2 shows an example of the reduction of metal artifacts in a CT image with an example embodiment of the proposed method.

FIG. 2 shows an example of the CT images generated with the method described in FIG. 1. Here, the schematically mapped hip bone structures 1 and thigh bone structures 2 are discernable in the images. A metallic artificial joint 3 has additionally been introduced into the right-hand thigh bone structure. The left-hand upper image was here recorded with a high tube voltage of 140 kV, the right-hand upper image with a tube voltage of 80 kV and shows a cross-section of the particular CT image data set. With lower x-ray energies the beam hardening effect is more clearly manifested, so that the beam-like image artifacts caused by the metallic artificial joint 3 are also more readily detectable in this image. The left-hand lower image here shows only the averaging of the two CT image data sets shown, that is to say a CT image at a medium x-ray energy, which lies between the two upper x-ray energies. Here too, the image artifacts caused by the artificial joint can clearly be discerned.

The lower right-hand image now shows the monoenergetic CT image newly calculated according to the proposed method at an energy of 120 keV. In comparison to the two upper original CT images, the reduction of the metal artifacts can be clearly discerned here. The method can be very simply executed, as it is performed on the basis of the image data, that is after the image reconstruction, and not on the basis of the raw data.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:
   generating at least two CT image data sets of an object volume with different medium x-ray energies;
   calculating a new CT image data set using a weighted combination of the at least two CT image data sets, wherein
     a weighting factor, used in the weighted combination, is selected such that image artifacts in the new CT image data set are relatively reduced compared with image artifacts in the at least two CT image data sets, the image artifacts being caused by metal within the object volume, and
     the new CT image data set is obtained through calculation of a monoenergetic CT image data set with an x-ray energy, the x-ray energy of the monoenergetic CT image data set being selected such that the image artifacts in the new CT image data set are relatively reduced compared with the image artifacts in the at least two CT image data sets; and
   changing the weighting factor, by a user, to bring about an interactive change in the x-ray energy of the monoenergetic CT image data set when examining one or more images of the new CT image data set, wherein the interactive change has an effect on the images of the new CT image data set represented in real time.

2. The method as claimed in claim 1, wherein basis material decomposition of the at least two CT image data sets is performed for the calculation of the monoenergetic CT image data set.

3. A tangible, non-transitory computer readable medium including program segments for, when executed on a computer device, causing the computer device to implement the method of claim 1.

* * * * *